United States Patent [19]

Pollak et al.

[11] Patent Number: 5,255,071
[45] Date of Patent: Oct. 19, 1993

[54] PHOTOREFLECTANCE METHOD AND APPARATUS UTILIZING ACOUSTO-OPTIC MODULATION

[76] Inventors: Fred H. Pollak, 531 Main St., New York, N.Y. 10044; Hong-En Shen, 7 Country Club Rd., Apt. 29, Eatontown, N.J. 07724

[21] Appl. No.: 406,726
[22] Filed: Sep. 13, 1989
[51] Int. Cl.⁵ .......................................... G01N 21/25
[52] U.S. Cl. .................... 356/417; 356/432
[58] Field of Search ............ 356/432, 432 T, 445, 356/446, 318, 417

[56] References Cited

U.S. PATENT DOCUMENTS

| | | | |
|---|---|---|---|
| 4,589,783 | 5/1986 | Thomas et al. | 356/432 T |
| 4,632,549 | 12/1986 | Czabaffy et al. | 356/326 |
| 4,765,742 | 9/1988 | Davinson | 356/373 |

OTHER PUBLICATIONS

Shen et al, "New Normalization Procedure for Modulation Spectroscopy," Rev. Sci. Instrum. vol. 58, #8, Aug. 1987, pp. 1429–1432.
Ginley et al, Photoelectrochemistry and Electrosynthesis on Semiconductor Materials, vol. 88-14 pp. 468–476 Jun. 3, 1988.

Primary Examiner—Davis L. Willis
Assistant Examiner—K. P. Hantis
Attorney, Agent, or Firm—Paul M. Craig, Jr.

[57] ABSTRACT

A method and apparatus for determining the characteristics of materials, particularly of semi-conductors, semi-conductor heterostructures and semi-conductor interfaces by the use of photoreflectance, in which monochromatic light and an acousto-optically modulated light beam reflected from the sample is detected to produce a d.c. signal and an a.c. signal, whereby the d.c. signal is applied to one input of a computer and the a.c. signal is used with another input of the computer which controls the light intensity of the monochromatic light impinging on the sample to maintain the d.c. signal substantially constant. The modulation frequency of the modulated pump beam and/or the wavelength of the monochromatic light can also be varied by the computer. Information about trap times can be obtained by determining the dependence of the in-phase signal on the pump modulating frequency, respectively.

20 Claims, 3 Drawing Sheets

PHOTOREFLECTANCE METHOD AND APPARATUS UTILIZING ACOUSTO-OPTIC MODULATION

FIELD OF INVENTION

The present invention relates to a method for determining the characteristics of materials, particularly of semiconductors, semiconductor heterostructures and semiconductor interfaces by the use of photoreflectance and to an apparatus for carrying out the method.

BACKGROUND OF THE INVENTION

The importance to study and characterize semiconductors (bulk or thin film), semiconductor heterostructures (superlattices, quantum wells, heterojunctions) and semiconductor interfaces (Schottky barriers, metal-insulator-semiconductors, semiconductor-electrolyte, semiconductor-vacuum, etc.) assumes ever-greater significance, particularly as many of these semiconductors and semiconductor microstructures are fabricated by modern thin-film techniques such as molecular beam epitaxy (MBE), metal-organic chemical vapor deposition (MOCVD), etc.

The materials and interfaces grown by MBE and MOCVD as well as other methods can be characterized by a variety of optical, electronic and structural methods including photoluminescence, photoluminescence excitation spectroscopy, absorption spectroscopy, modulation spectroscopy, Raman and resonant Raman scattering, cyclotron resonance, Hall effect, transmission electron microscopy, etc. Each of these tools provides specific information about the material of interest. For characterization purposes the experimental tools should be as simple and informative as possible. Many of the methods mentioned above are specialized and sometimes difficult to employ. Because of its simplicity and proven utility, photoreflectance has recently gained importance for the evaluation of semiconductor thin films and heterostructures.

In modulation spectroscopy in which the derivative with respect to some parameters is evaluated, uninteresting background structure is eliminated in favor of sharp lines corresponding to specific transitions between energy levels in the semiconductors and semiconductor microstructures. Also, weak features that may not have been seen in the absolute spectra are enhanced. While it is difficult to calculate a full reflectance (or transmittance) spectrum, it is possible to account for the lineshape of localized spectral features of modulation spectroscopy. The ability to fit the lineshape is an important advantage of modulation spectroscopy. Lineshape fits yield accurate values of the semiconductor energy gap as well as of the broadening parameter. In addition, since "external" modulation spectroscopy is the a.c. response of the system to the modulating parameter, photoreflectance also provides information in the other modulation variables such as phase, modulation frequency, modulation amplitude, modulation wavelength.

In photoreflectance, the built-in electric field of the materials is modulated by the photo-injection of electron-hole pairs created by a pump beam of wavelength $\lambda_p$ which is chopped at frequency $\Omega_m$. Experiments have indicated that photoreflectance is due to the modulation of the built-in electric field through a recombination of the minority species with charge in traps. Thus, by measuring the dependence of the photoreflectance signal on $\Omega_m$ it is possible to gain information about trap times with the use of photoreflectance.

Photoreflectance, a contactless form of electromodulation, has been found to be a powerful tool to study the interface electric field distribution in semiconductor structures. In photoreflectance, the electric field in the material is modulated by the photo-injection of electron-hole pairs by a pump beam chopped at frequency $\Omega_m$. It has already been demonstrated that photoreflectance is a form of electroreflectance yielding sharp, derivative-like spectra in the region of interband transitions in bulk or thin film semiconductors. Since photoreflectance is the a.c. response of the system to the modulating electric field, there is also important information in the other modulation parameters such as modulation frequency ($\Omega_m$), pump beam wavelength ($\lambda_p$), pump beam intensity ($I_p$), etc.

In a photoreflectance apparatus as disclosed in our copending application Ser. No. 07/382,191, filed Jul. 20, 1989 and entitled "Method and Apparatus for Determining a Material's Characteristics by Photoreflectance," the subject matter of which is incorporated herein by reference, a mechanical chopper was used to modulate the pump beam. However, the modulation frequency $\Omega_m$ was limited to about 4,000 Hz. It has now been discovered that by varying both pump beam wavelength $\lambda_p$ and the modulation frequency $\Omega_m$ up to a value of 100 KHz by the use of an acousto-optical modulator, it is possible to identify the component layers, their quality and the properties of the various interfaces.

The present invention is therefore concerned with further improving the prior art apparatus to achieve improved results on the materials' determination and to gain additional information on the characteristics of the materials examined with greater accuracy and reliability.

Accordingly, it is an object of the present invention to provide an improved method and apparatus for determining the characteristics of certain materials by photoreflectance which avoid by simple means the shortcomings encountered with the prior art apparatus and methods in the use thereof.

Another object of the present invention resides in an improved apparatus which permits determination of the characteristics of semi-insulating substrates and of undoped buffer layers and of the interface states therebetween.

A further object of the present invention resides in an apparatus utilizing photoreflectance for characterizing conductivity or semi-insulating structures as found, for example, in enhancement mode MESFET and HEMT devices.

Still another object of the present invention resides in an apparatus which can be used for in-situ characterization of epigrown surfaces and interfaces.

Another object of the present invention resides in a method for determining characteristics of certain materials, such as semiconductor materials and semiconductor heterostructures, which is simple in use, reliable in its operation and accurate in the results obtained therewith.

Still another object of the present invention resides in a method based on photoreflectance which permits continuous in-situ monitoring of the manufacture of materials, such as semiconductor materials, that eliminates the shortcomings and drawbacks encountered with the prior art systems.

A further object of the present invention resides in a method based on photoreflectance which permits accurate quality control in the manufacture of semiconductor materials.

BRIEF DESCRIPTION OF THE DRAWINGS

These and other objects, features and advantages of the present invention will become more apparent from the following description when taken in connection with the accompanying drawing which shows, for purposes of illustration only, one embodiment in accordance with the present invention, and wherein.

DETAILED DESCRIPTION OF THE DRAWINGS

Figure 1:
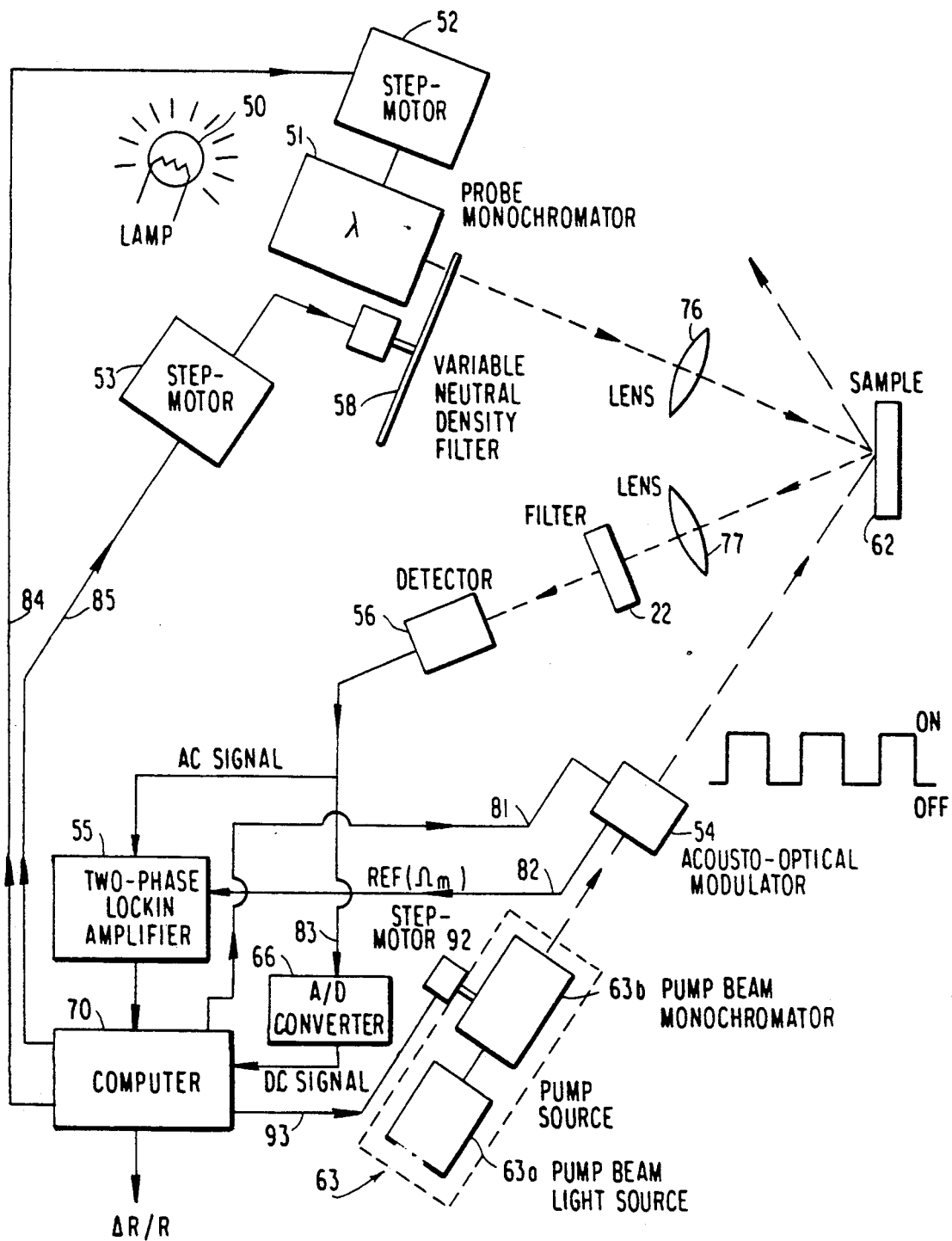
FIG. 1 is a schematic block diagram of an apparatus in accordance with the present invention which utilizes photoreflectance in combination with acousto-optical pump beam modulation which is computer-controlled to increase accuracy and versatility of the equipment.

Referring now to the drawing, and more particularly to FIG. 1, reference numeral 50 designates an appropriate lamp source such as a Xenon arc light source, whose light passes through a monochromator 51, to be referred to hereinafter also as probe monochromator. The exit intensity of the monochromator 51 at the wavelength $\lambda$ is focused onto a sample 62. $I_o(\lambda)$ is thereby the intensity of light from the probe source 50, 51 striking the sample 62. Electromodulation of the sample 62 is produced by photoexcitation of electron-hole pairs created by a pump beam from a pump source generally designated by reference numeral 63. The pump beam can be a laser or preferably a light source 63a and a second monochromator 63b and, in contrast to the mechanical chopper used heretofore, is modulated in accordance with the present invention by an optical modulator 54 of conventional construction at a frequency $\Omega_m$. The use of such an acousto-optical modulator, for example, as manufactured by Newport Electro Optics Systems, Inc. permits modulation frequencies up to about 5 MHz. The beam reflected from the sample 62 is focused onto a detector 56, such as a photomultiplier, photodiode, photoconductor, etc. The output of the detector 56 contains two signals, i.e., the d.c. signal and the a.c. signal. Although FIG. 1 shows the configuration for reflectance, the experiment can also be readily modified for transmission by placing the detector behind the sample. Accordingly, the term photoreflectance (PR) is used in this application in a broad sense to encompass both reflectance and transmittance.

The probe monochromator 51 is driven by step-motor 52 which is controlled by the computer generally designated by reference numeral 70 of any conventional construction, programmed by conventional techniques to achieve the various functions, as will be described more fully hereinafter. The variable neutral density filter 58 is also driven by a step-motor 53 which is also controlled by the computer 70. It has been found that the signal-to-noise ratio can be improved by a factor of 10 using such step-motor control. In addition, the computer 70 also controls the frequency ($\Omega_m$) of the acousto-optical modulator 54, modulating the pump beam emitted by the pump source 63 which may be a He-Ne laser or preferably a light source 63, such as a Xenon arc lamp and a second monochromator 63b. Furthermore, the lock-in amplifier 55 is a two-phase model of known construction which determines the in-phase and out-phase components of the photoreflectance signal (relative to the pump beam). The use of the two-phase lock-in amplifier 55 is important for evaluating the photoreflectance signal as a function of $\Omega_m$ to yield information about trap states as will be discussed more fully hereinafter. It has also been found that signals from different depth regions of a sample structure produce signals with different phases and dependence on $\Omega_m$ which can be sorted out by the two-phase lock-in amplifier 55 and the computer-controlled modulating frequency $\Omega_m$.

In FIG. 1, the probe light produced by lamp 50 in conjunction with the probe monochromator 51, which can be adjusted by step-motor 52 to vary the wavelength $\lambda$ of the probe light, is directed onto sample 62 by the use of a lens(es) or mirror(s), schematically indicated by lens 76. The pump beam produced by the pump source 63, whose wavelength $\lambda_p$ can be varied by means of the second monochromator 63b, is also directed onto the sample 62 after being modulated by the acousto-optical modulator 54 whose frequency $\Omega_m$ can be varied by computer 70 by way of line 81. The pump beam wavelength $\lambda_p$ is also controlled by computer 70 by way of a line 93 utilizing a step-motor 92 in a manner similar to the control of the wavelength $\lambda$ of the probe-light. The light reflected (transmitted) from the sample 62 is directed onto detector 54 by a lens(es) or mirror(s), schematically indicated by lens 77. A filter 22 may be interposed in the optical path between the sample 62 and detector 54. The a.c. signal in the output of detector 54 is applied to the input of the two-phase lock-in amplifier 55 to which is also applied a reference signal ($\Omega_m$) from the modulator 54 by way of line 82 to provide information about the modulating frequency $\Omega_m$ for purposes which will be explained hereinafter. The d.c. signal from detector 54 is applied to computer 70 by way of line 83 which includes an A/D converter 66 to change the analog signal from detector 54 into a digital signal for use by the computer 70.

One output of computer 70 contains the desired photoreflectance signal $\Delta R/R$ which is applied to a user-friendly display, e.g. the display screen (not shown) associated with the computer. Another output of computer 70 controls the step-motor 52 to vary the probe-light wavelength $\lambda$, by way of line 84. A further output of computer 70 controls the step-motor 53 to vary the adjustment of the variable neutral-density filter 58 by way of line 85, and still another output of computer 70 controls the frequency $\Omega_m$ of the modulator 54 by way of line 81, and still another output of computer 70 controls the pump beam wavelength $\lambda_p$, all for purposes to be explained more fully hereinafter.

The light striking the detector 56 contains two signals: the d.c. (or average value) is given by $\beta(\lambda)I_o(\lambda)R(\lambda)$ $[\beta(\lambda)I_o(\lambda)T(\lambda)]$, where $\beta(\lambda)$ is the optical response of the collecting lens (or mirror), $R(\lambda)[T(\lambda)]$ is the d.c. reflectance (transmittance) of the material while the modulated value at frequency $\Omega_m$ is check $\alpha$or $\beta\alpha(\lambda)I_o(\lambda)\Delta R(\lambda)[\alpha(\lambda)\Delta T(\lambda)]$, where $\Delta R(\lambda)[\Delta T(\lambda)]$ is the modulated reflectance (transmittance). The a.c. signal from the detector 56, proportional to $\alpha I_o \Delta R(\alpha I_o \Delta T)$ is measured by the lock-in amplifier 55. The a.c. and d.c. signals from the detector 56 are denoted as $V_{ac}$ and $V_{dc}$, respectively.

In order to evaluate the quantity of interest $\Delta R(\lambda)/R(\lambda)[\Delta T(\lambda)/T(\lambda)]$ a normalization procedure must be used to eliminate the uninteresting common feature $\alpha I_o$. In FIG. 1, normalization is achieved by the use of the variable neutral density filter 58 connected to the step motor 5 driven by computer 70. The variable neutral density filter 58 is placed in the optical path between the probe monochromator 51 (or other probe source such as a dye laser) and the sample 62. The d.c. signal from the detector 56 ($V_{dc}$) is fed by way of A/D converter 66 to the computer 70 which varies the variable neutral density filter 58 and hence $\alpha(\lambda)I_o(\lambda)$ in order to keep $V_{dc}$ as a constant. Thus, in this procedure, the operating conditions of the experiment, i.e., detector amplification, instrumental resolution, etc. are kept constant.

In photoreflectance, problems are caused by (a) diffuse reflected light from the pump source and (b) photoluminescence produced by the pump light getting into the detector 56. This latter problem is particularly acute at low temperatures (semiconductor and semiconductor structures) and for check K superlattices and quantum wells even at 77 K and sometimes room temperature. A main goal in a photoreflectance measurement is therefore to eliminate diffuse reflected light from the modulation source and/or photoluminescence produced by the intense pump light. Both of them may reach the detector 56 and then produce a spurious signal in the lock-in amplifier 55. The filter 22 in front of the detector 56 assists in reducing the diffused light from the pump source.

The d.c. output of the photodetector 56, $V_{dc}$, can be written as:

$$V_{dc} = \alpha(\lambda) I_o(\lambda) R(\lambda) K(\lambda) A(\lambda) \quad (1)$$

where $K(\lambda)$ is the detector response (including the response of a filter if it is used) and $A(\lambda)$ is the amplification factor of the detector.

In photoreflectance, the a.c. output ($V_{ac}$) is given by:

$$V_{ac} = [\alpha(\lambda) I_o(\lambda) R(\lambda) K(\lambda + \alpha(\lambda_{sp}) I_{sp}(\lambda_{sp}) K(\lambda_{sp})] A(\lambda) \quad (2)$$

where $I_{sp}$ is the intensity of the spurious signal due to scattering and/or photoreflectance and $\lambda_{sp}$ is the wavelength of the spurious signal.

In the normalization procedure of FIG. 1, the quantity $V_{dc}$ is kept at some constant value C by varying $I_o(\lambda)$, the light intensity incident on the sample 62, by means of the variable neutral density filter 58. In such a procedure, the amplification of the detector 56 is not changed and hence $A(\lambda) = A$, where A is a constant. Thus, we can write $$\alpha(\lambda) I_o(\lambda) = C/R(\lambda) K(\lambda) A \quad (3)$$

Substituting Equation (3) into Equation (2) yields for $S_{LIA}(= V_{ac}/V_{dc})$, the normalized output signal from the lock-in amplifier 55, the term:

$$S_{LIA} = [C \Delta R(\lambda)/R(\lambda)] + [\alpha(\lambda_{sp}) I_{sp}(\lambda_{sp}) K(\lambda_{sp}) A] \quad (4)$$

Since $\alpha(\lambda_{sp})$, $I_{sp}(\lambda_{sp})$, $K(\lambda_{sp})$ and A are all independent of the probe wavelength, the second term in Equation (4) is a constant. If this second term is not too large in relation to $C \Delta R/R$, it is fairly simple to subtract the spurious factor and recover the true signal $\Delta R/R$. It has been found that if $C \Delta R/R > 0.01(\alpha I_{sp} K A)$, the subtraction can be readily accomplished. The subtraction of the spurious signal is important for proper operation of the photoreflectance apparatus.

COMPUTER FUNCTIONS

The computer 70 of any known type and with sufficient memories is programmed to provide the following functions. Since the programming involves conventional programming techniques, as known to persons skilled in the art, a detailed description thereof is dispensed with herein for the sake of simplicity.

The software used with computer 70 can be divided into three general functions which can be designated as (A) Control and Data Acquisition, (B) Data Analysis including lineshape fit of photoreflectance spectra and (C) Comparison of Relevant Parameters obtained from the Data Analysis with Theoretical Models.

A. Control/Data Acquisition Component

The control/data acquisition component serves the following functions:

(1) It controls the step-motor 53 which, in turn, varies the variable neutral density filter 58 in order to keep $V_{dc}$ as a constant for normalization purposes. This is preferably done as described in our continuation-in-part application Ser. No. 07/408,903, filed on even date with this application and entitled "Method and Apparatus for Determining a Material's Characteristics by Photoreflectance Using Improved Computer Control," the subject matter of which is incorporated herein by reference.

(2) It controls the step-motor 52 which drives the probe monochromator 51. Thus, the range of wavelength $\lambda$ for a given experiment can be set by the computer 70. Also, the computer 70 can control the step-motor 52 for multiple scans to accumulate a preset signal-to-noise ratio.

(3) The computer 70 records both the in-phase and out-phase components of the signal from the lock-in amplifier 55.

(4) The computer controls the chopping frequency $\Omega_m$. When measuring the dependence of the in-phase signal on $\Omega_m$, the computer 70 controls $\Omega_m$. In this case the amplification of the electronic system (detector, pre-amplifier, lock-in amplifier) may change with $\Omega_m$. The computer software automatically corrects for this.

(5) The computer controls the step-motor 92 which drives the second monochromator 63b to change the pump-beam wavelength $\lambda_p$.

(6) The computer control of a given experiment is an important function in the subtraction of the spurious signal $\alpha I_{sp} K A$ from the true photoreflectance signal $C(\Delta R/R)$. This is accomplished in the following manner. At a given probe beam wavelength ($\lambda$), which the computer 70 sets by means of step-motor 52, the computer sets the variable neutral density filter 58 for maximum density. Thus, the constant C (and $I_o$) in Equations (3) and (4) is made equal to zero. In this case $S_{LIA}(\lambda) = \alpha I_{sp} K A$. This signal is analyzed by the computer 70 to determine the absolute phase of the pump beam appearing at the input terminal of the lock-in amplifier 55. Then the computer sets the lock-in amplifier 55 to the correct phase with respect to the optical pump and offsets the spurious signal by changing the zero setting of the lock-in amplifier 55. In the case of large spurious signals, this procedure is repeated at several different probe beam wavelengths.

B. Data Analysis/Fit

This component performs the following functions:

(1) It interfaces with components A and C.

(2) It presents the data (photoreflectance spectrum) on the computer screen in a user-friendly manner. For example, photon wavelength is converted to photon energy. Different spectral regions of the data can be presented in magnified form.

(3) It provides data transformation including Fast Fourier Transform, filtering and smoothing procedures to improve signal-to-noise ratio and derivatives and integrals to analyze signals.

(4) It provides lineshape fit to data to extract important parameters such as photon energy of spectral features, linewidth of spectral feature, amplitude and phase. This is an important aspect of the entire program.

(5) It fits to the dependence of the in-phase photoreflectance signal on chopping the frequency ($\Omega_m$). This fit can be used to obtain information about trap times.

(6) It provides vector analyses of the in-phase and out-phase components of a spectrum to distinguish signals from different depth regions of the sample.

(7) If Franz-Kaldysh oscillations are observed, it evaluates peak positions of the Franz-Kaldysh oscillations. This can be used to determine electric fields and sometimes carrier concentration.

C. Comparison of Relevant Parameters of Data with Theoretical Models

In software component B, various pieces of experimental information are obtained such as positions of energy gaps, peak positions of Franz-Kaldysh oscillations, etc. In order to make this data useful, it must be compared with various models to give the user information about the semiconductor or semiconductor structure.

(1) In thin film or bulk alloy materials, the position of the energy levels can be used to evaluate alloy composition. For example, in $Ga_{1-x}Al_xAs$ the Al composition (x) can be determined.

(2) In thin film or bulk elemental or binary semiconductors (GaAs, Si, etc.) the position of the energy gap can be used to determine the temperature of the material.

(3) From the evaluation of linewidth one can gain information about crystal quality.

(4) Strains can be determined from shifts and splittings of peaks.

(5) If Franz-Kaldysh oscillations are observed, positions of peaks can be used to evaluate the built-in electric field and in some cases carrier concentrations.

(6) From the dependence of the in-phase component on $\Omega_m$ and temperature T, one can evaluate activation energy of trap states.

(7) In semiconductor microstructures such as superlattices, quantum wells and multiple quantum wells a complex theoretical model can be compared to the experimentally determined energy gap to evaluate width of quantum wells and barriers, barrier height and in the case of lattice-mismatched systems (InGaAs), the built-in strain.

There is frequently a strong interaction between this aspect of the program and the lineshape fit discussed in software component B-4 above. In semiconductor microstructures the spectrum is often very complex and hence only major peaks will be fitted by the lineshape fit of software component B-4. This initial information is then fed into the theoretical model of software component C-7 to determine where other smaller features should be found. This information is then introduced into software component B-4 to complete the lineshape fit of the minor spectral features.

A. In-situ Monitoring of Growth Conditions for MBE and MOCVD

Photoreflectance can be performed on GaAs and $Ga_{0.82}Al_{0.18}As$ at temperatures up to 600° C. These temperatures correspond to growth conditions for MBE and MOCVD. Thus by using photoreflectance the temperature of the GaAs substrate can be measured in a contactless manner to about ±10° C. to within a depth of only a few thousand Angstroms, i.e., near the growth surface. Also, in situ monitoring of the growth of epitaxial layers of $Ga_{1-x}Al_xAs$ can be performed. In both cases topographical scans can be performed to evaluate uniformity. The energy band gaps of semiconductors are functions of various parameters such as temperature, alloy composition (in the case of alloy semiconductors such as $Ga_{1-x}Al_xAs$), stress, etc. Thus by accurately measuring the position of the energy gap one can gain information about these quantities.

B. Electric Field Distributions At Semiconductor Heterostructive Interfaces

Photoreflectance can also be used as a contactless method to study electric field distributions and trap times at semiconductor heterostructure interfaces. The electric field distributions and trap times can be related to charges at the interfaces. The knowledge of the properties of these charges is very important for device applications.

Use is thereby made not only of the sharp, derivative-like features of photoreflectance but two new important aspects are also employed, i.e., the use of different pump wavelengths ($\lambda_p$) and modulating frequency ($\Omega_m$) dependence of the in-phase component of the photoreflectance signal. This permits investigation, for example, of the photoreflectance spectra at 300 K from an MBE grown $Ga_{0.83}Al_{0.17}As/GaAs/GaAs$ (epilayer/buffer/substrate) heterostructure as a function of $\lambda_p$ (8200 A°–4200 A°) and $\Omega_m$ (20Hz–100 kHz). The buffer is semi-insulating GaAs. The sharp spectral features permit to observe the direct band gaps of the different parts of the structure, i.e., epilayer, buffer, substrate.

By using different $\lambda_p$, carriers can be photo-excited in different regions of the structure and hence these separate sections can be selectively modulated.

By measuring the dependence of the in-phase component of the photoreflectance signal as a function of $\lambda_m$ it is possible to determine trap times at the various interfaces. The in-phase aspect is of importance for the following reason. Heretofore trap times were deduced from the dependence of the magnitude of the photoreflectance signal on $\Omega_m$. The magnitude of the signal is the sum of the squares of the in-phase and out-phase signals. However, this quantity does not obey the principle of superposition if there are contributions from traps of different time constants. Thus, it is rigorously correct for only a single trap state. For a multiple trap state it is necessary to evaluate the $\Omega_m$ dependence of the in-phase component (with respect to the pump beam) in order to employ the superposition of different trap time contributions.

The computer control of the pump-modulating frequency $\Omega_m$ as well as the accumulation of the in-phase (as well as out-phase) component of the signal is highly important for the success of such an experiment.

Figure 3:
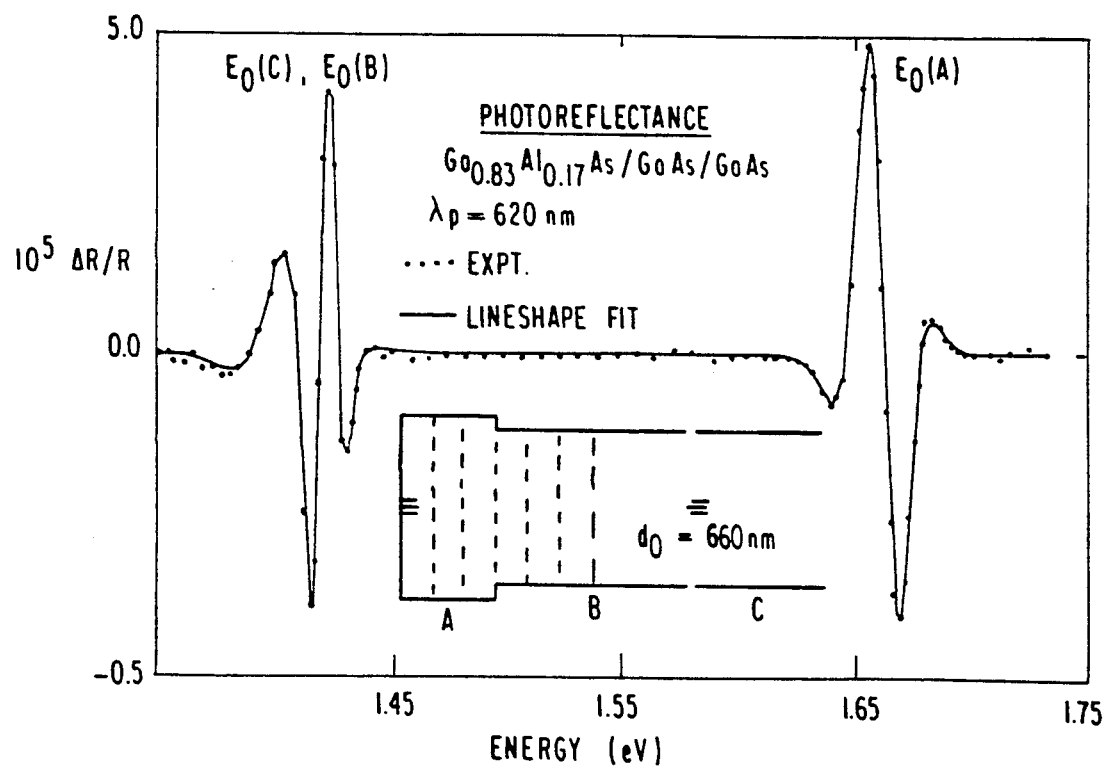
FIG. 3 is a diagram illustrating photoreflectance signal versus photon energy for a GaAlAs/GaAs/GaAs structure for a pump beam wavelength of 620 nm.

The direct band gaps of the various components of a structure are designated $E_o(A)$, $E_o(B)$ and $E_o(C)$ for the GaAlAs epilayer (region A), GaAs buffer (region B) and GaAs substrate (region C), respectively. For 420 nm pump radiation (FIG. 4), which does not penetrate into either region B or C, $E_o(A)$ and $E_o(B)$ could be observed but not $E_o(C)$. All three peaks are seen from $\lambda_p = 620$ nm (FIG. 3), which corresponds to an energy larger than $E_o(A)$ and penetrates into region B but not into region C. When the pump photon energy (1.51 eV) is well below $E_o(A)$, photoexcited electron-hole pairs are created in both the Ga As buffer and substrate regions. In this case the spectrum exhibits primarily $E_o(C)$ with a small contribution from $E_o(B)$ (FIG. 3). In addition $E_o(A)$ and $E_o(C)$ have different variations with $\Omega_m$; the dependence of $E_o(B)$ is related mainly to the modulation mechanism of region A with some contribution from region C. These results are evidence for a low density of interface states between the GaAs buffer layer and the GaAlAs epilayer and relatively large density of states between the substrate and buffer.

The following is a typical experimental procedure used with the present invention.

The heterostructure used consisted of a 200 nm $Ga_{0.83}Al_{0.17}As$ epilayer grown on a 800 nm GaAs buffer on a semi-insulating (SI) <100> LEC GaAs substrate. All measurements were made at 300 K. The source for $\lambda_p$ was a Xenon arc filtered by a ¼ meter monochromator as well as a He-Ne laser. The intensity of the pump beam was about 2 mW. In all cases the observed lineshapes were independent of $I_p$ indicating modulation in the low-field regime. A two-phase lock-in amplifier was used to record the in-phase and out-phase components of the photoreflectance signal relative to the phase of the pump beam. Measurements using the 633 nm line of the He-Ne laser were made up to 100 kHz using an acousto-optic modulation instead of a mechanical chopper.

Figure 2:
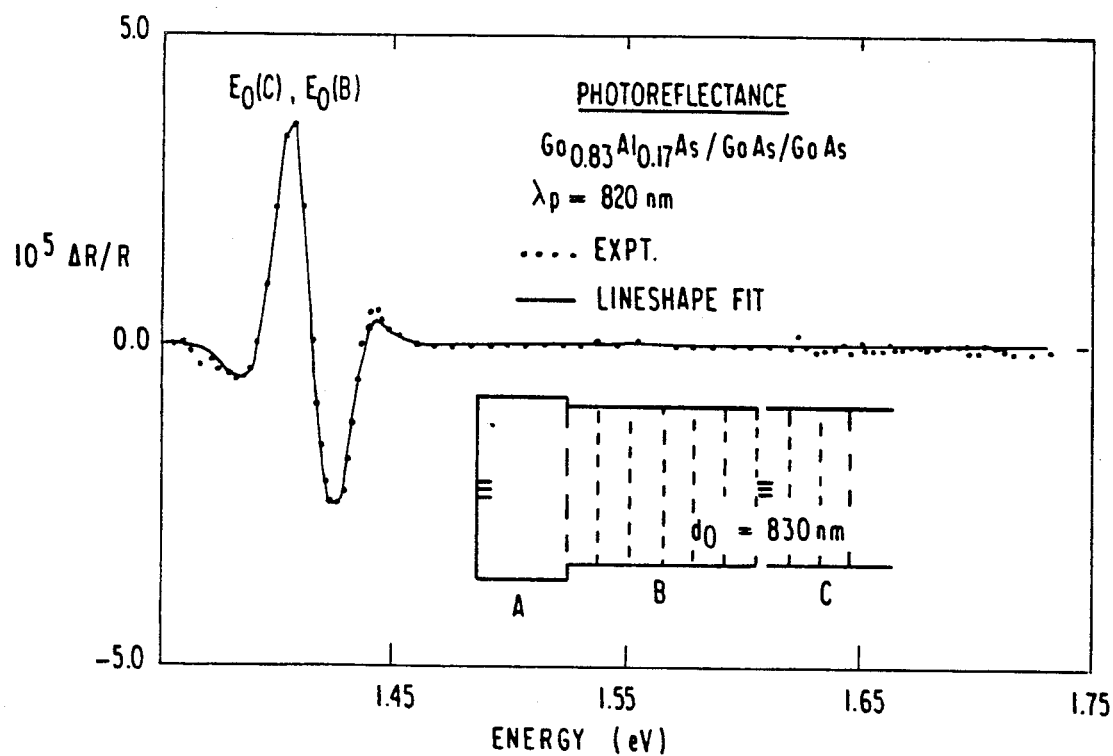
FIG. 2 is a diagram illustrating photoreflectance signal versus photon energy for a GaAlAs/GaAs/GaAs structure for a pump beam wavelength of 820 nm.

The dotted line in FIG. 2 is the experimental photoreflectance spectrum with $\lambda_p = 820$ nm and $\Omega_m = 200$ Hz. For this value of $\lambda_p$ the GaAlAs is transparent and the penetration depth ($d_o$) in GaAs is 830 nm. The configuration of the A, B and C regions of the sample as well as the region of absorption of $\lambda_p$ (dashed vertical lines) are shown schematically in the lower portion of this figure. The solid line is a least-squares fit to the first derivative of a Gaussian lineshape function. Such a functional form is appropriate for bound states, such as excitons, at room temperature.

The spectrum of FIG. 2 exhibits structure in the vicinity of the direct band gap of GaAs, but no signal is observed in the region of the GaAlAs gap. The lineshape fit indicates that there are two oscillators, denoted as $E_o(C)$ and $E_o(B)$, the latter being only about 18% of the former. The energies and broadening parameters are 1.413 eV, 11 meV and 1.420 eV, 4 meV for $E_o(C)$ and $E_o(B)$, respectively. The features $E_o(C)$ and $E_o(B)$ originate in the GaAs substrate and buffer, respectively. The narrower linewidth for the latter peak is probably attributable to the better quality of MBE grown material in relation to bulk GaAs.

The dotted line in FIG. 3 is the experimental photoreflectance spectrum for $\lambda_p = 620$ nm and $\Omega_m = 200$ Hz. In this case $d_o$(GaAlAs)=420 nm and $d_o$(GaAs)=240 nm. Thus, electron-hole pairs are created in regions A and B but not in region C as shown schematically by the dashed vertical lines. The solid line is again a least-square fit to the first-derivative of a Gaussian profile. In addition to $E_o(C)$ and $E_o(B)$, which have a ratio of about ⅓, $E_o(A)$ is also noted at an energy of 1.662 eV with a linewidth of about 8 meV. The position of $E_o(A)$ enables determination of the Al composition.

Figure 4:
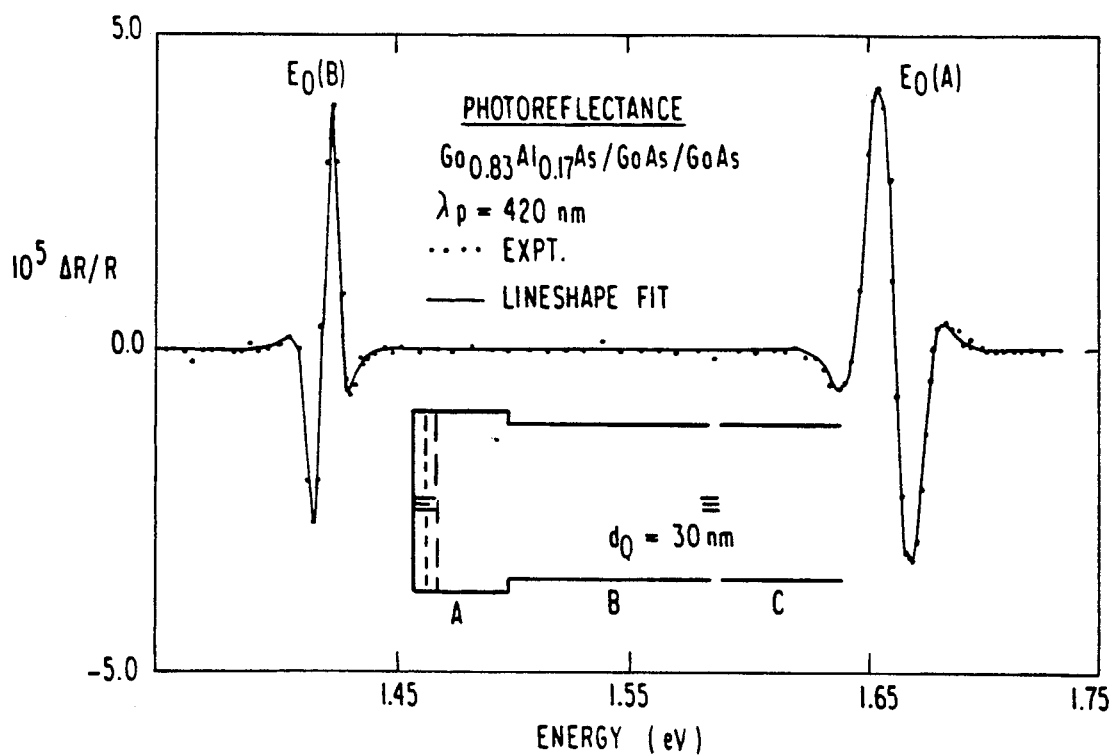
FIG. 4 is a diagram illustrating photoreflectance signal versus photon energy for a GaAlAs/GaAs/GaAs structure for a pump beam wavelength of 420 nm.

The data for $\lambda_p = 420$ nm and $\Omega_m = 200$ Hz is shown by the dotted line in FIG. 4. Since $d_o$(GaAlAs)=30 nm for this pump wavelength, photoexcited carriers are created only in region A and not in regions B or C. The solid line is again a least-square fit to the first derivative of a Gaussian lineshape form. Only two peaks, $E_o(B)$ and $E_o(A)$, are observed under these conditions. No substantial evidence exists for $E_o(C)$ in the lineshape around 1.42 eV.

Figure 5:
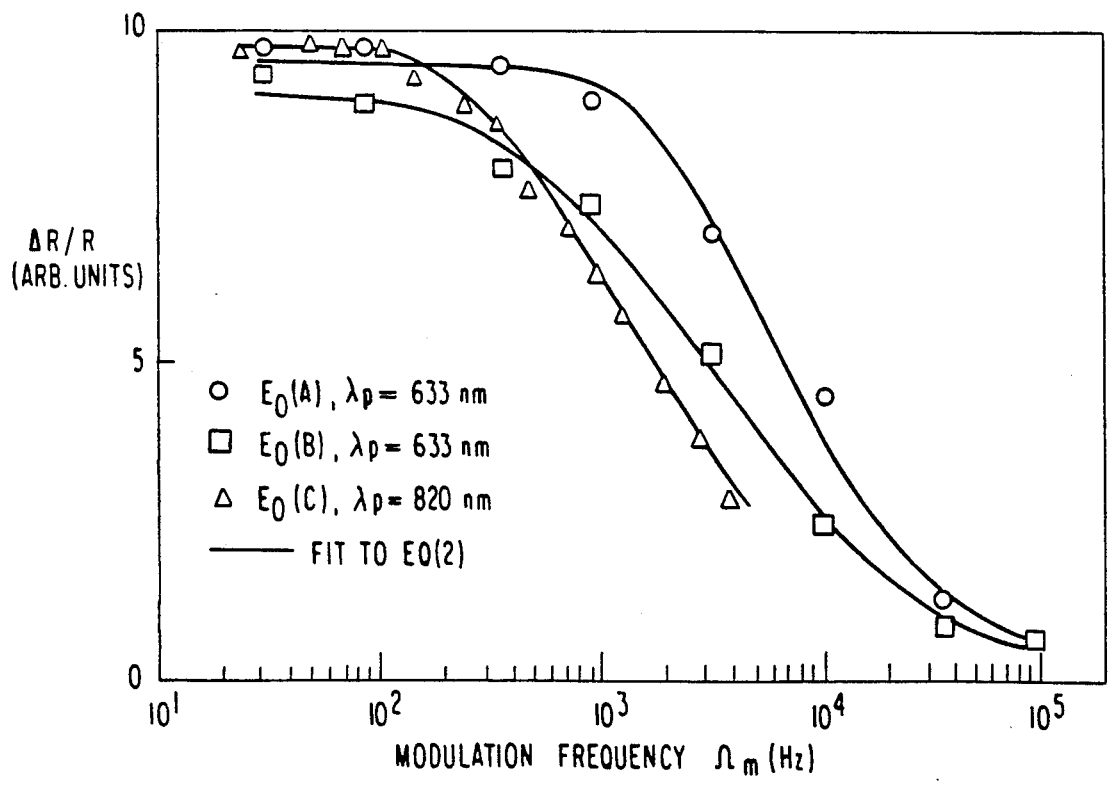
FIG. 5 is a diagram illustrating photoreflectance signal versus pump beam modulation frequency, $106_m$.

The modulation frequency ($\Omega_m$) dependence of the amplitude of the in-phase component of the various photoreflectance structures is plotted in FIG. 5. The variation of $E_o(A)$ and $E_o(B)$ was evaluated from the spectrum produced by the 633 nm pump radiation from a He-Ne laser and an acousto-optic modulator as chopper. The spectrum for $\lambda_p = 633$ nm is very similar to that of FIG. 3. Since the feature around 1.42 eV has a contribution from $E_o(B)$ that is three times larger than $E_o(C)$, the $\Omega_m$ dependence of $E_o(B)$ has been evaluated from the high energy side (1.43 eV) of this structure.

The dependence of $\Delta R/R$ on $\Omega_m$ can be accounted for on the basis of the following considerations. The chopped (modulated) pump radiation can be considered as a square wave source. When light impinges on the sample, electron-hole pairs are created These charges are then free to fill traps and modify the electric field strength. Presumably these excess carriers change the built-in field in a response time much faster than the shortest characteristic time of the used modulation. When the light is switched off, the trap population and hence electric-field strength are restored with a characteristic time $\tau$. For a chopping frequency $\Omega_m$ it can be shown that the Fourier transform of the in-phase component of the photoreflectance intensity, $[\Delta R(\Omega_m)/R]_{in-phase}$, is given by:

$$[\Delta R(\Omega_m)/R]_{in-phase} = \sum_{i=1}^{n} [\Delta R(O)/R]_i f(\Omega_m \tau_i) \quad (5a)$$

$$f(\Omega_m \tau_i) = \{1 + 2\pi^2(\Omega_m \tau_i)^2[1 - \exp(-\tfrac{1}{2}\Omega_m \tau_i)]\}/[1 + 4\pi^2(\Omega_m \tau_i)^2] \quad (5b)$$

when $\tau_i$ is the characteristic time constant of the $i^{th}$ trap state and $[\Delta R/(0)/R]_i$ is the photoreflectance signal produced by the modulation of the $i^{th}$ trap state in the limit of $\Omega_m \tau_i << 1$. It can be shown that in order to employ the principle o superposition of the contribution of states with different trap times it is necessary to consider the in-phase component of $\Delta R(\Omega_m)/R$, not the amplitude.

The solid lines in FIG. 5 are least-squares fits of Equations (5a and 5b) to the experimental data. The $E_o(A)$ feature contains a contribution from only one time constant, $\tau_1(A) = 0.047$ ms. This time constant was too fast to be observed for a modulation frequency $\Omega_m$ limited to 4,000 Hz because of the limitations of the mechanical chopper., The behavior of $E_o(C)$ is also determined by only one time constant with $\tau_1(C)=0.33$ ms. However, $E_o(B)$ contains contributions from two trap mechanisms with $\tau_1(B)=0.045$ ms and $\tau_2(B)=0.37$ ms. The ratio of the two contributions $[\Delta R(0)/R]_1/[\Delta R(0)/R]_2=1.6$. Thus, the main mechanism for the modulation of the GaAs buffer layer is from the fast states $[\tau_1(B)=0.045$ ms$]$ associated with the GaAlAs with some contribution from the slower state. The latter is the modulation mechanism for $E_o(C)$ and probably originates in the interface states between the buffer and substrate.

The photoreflectance technique has thus been usable to characterize an undoped GaAlAs/GaAs/GaAs heterostructure. By varying both the wavelength of the pump beam and its modulation frequency, it is possible to identify the component layers, their quality and the properties of the various interfaces. By using an acousto-optic modulator, measurements up to 100 kHz are possible, which in turn allows obtaining information about trap states with time constants as fast as about 40 $\mu$s. The technique according to this invention as applied to undoped or low conductivity structures is thus complementary to electrical modulation techniques, e.g. electroreflectance, DLTS, etc., which are usually applied to conducting structures.

While we have shown and described only one embodiment in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

We claim:

1. An apparatus for determining characteristics of materials by photoreflectance, comprising monochromatic light source means, means for directing the monochromatic light onto a sample to be examined, pump beam means for directing a beam of energy onto the sample including acousto-optical modulation means for modulating said beam at frequencies above those attainable by mechanical modulation, means for directing at least a part of the non-absorbed monochromatic light and of the non-absorbed modulated beam from the sample onto a detector means operable to produce a d.c. signal and an a.c. signal in its outputs, computer means, means for applying the d.c. signal from the detector means to an input of the computer means, a lock-in amplifier means receiving at its input the a.c. signal from the detector means and operatively connected with its output to another input of the computer means, and control means for keeping the substantially constant the operating conditions in a given experiment including variable means for varying the light intensity of the monochromatic light impinging on the sample and actuating means for controlling the variable means by an output from the computer means to maintain the d.c. signal substantially constant.

2. An apparatus according to claim 1, wherein said variable means includes a variable neutral density filter, and wherein said actuating means includes a stepping motor controlled from the corresponding computer output.

3. An apparatus according to claim 2, further comprising means for controlling the modulation frequency of said acousto-optical modulation means from said computer means.

4. An apparatus according to claim 3, further comprising means for changing the wavelength of the pump beam.

5. An apparatus according to claim 4, wherein the computer means is operable to control the wavelength of the pump means.

6. An apparatus according to claim 5, further comprising means for changing the wavelength of the monochromatic light from said light source means by said computer means.

7. An apparatus according to claim 6, wherein the means for changing the wavelength of the monochromatic light includes a stepping motor means controlled by said computer means and operable to change the wavelength of the monochromatic light.

8. An apparatus for determining characteristics of materials by photoreflectance, comprising monochromatic light source means, means for directing the monochromatic light onto a sample to be examined, pump beam means for directing a beam of energy onto the sample including acousto-optical modulation means for modulating said beam at frequencies above those attainable by mechanical modulation, means for directing at least a part of the non-absorbed monochromatic light and of the non-absorbed modulated beam from the sample onto a detector means operable to produce a d.c. signal and an a.c. signal in its outputs, computer means, means for applying the d.c. signal from the detector means to an input of the computer means including an A/D converter, a two-phase lock-in amplifier means receiving at its output the a.c. signal from the detector means and operatively connected with its output to another input of the computer means, an control means for keeping substantially constant the operating conditions in a given experiment including variable means for varying the light intensity of the monochromatic light impinging on the sample and actuating means for controlling the variable means by an output from the computer means to maintain the d.c. signal substantially constant.

9. An apparatus according to claim 8, further comprising means for controlling the modulation frequency of said acousto-optical modulation means from said computer means.

10. An apparatus according to claim 8, further comprising means for changing the wavelength of the monochromatic light by said computer means.

11. An apparatus according to claim 10, wherein the means for changing the wavelength of the monochromatic light from said light source means includes a stepping motor means controlled by said computer means and operable to change the wavelength of the monochromatic light.

12. An apparatus according to claim 11, further comprising means for controlling the modulation frequency of said acousto-optical modulation means from said computer means.

13. An apparatus according to claim 8, wherein said variable means includes a variable neutral density filter, and wherein said actuating means includes a stepping motor controlled from the corresponding computer output of the computer means in such a manner that the stepping motor is rapidly actuated in predetermined multiple steps until it overshoots the light intensity required for the constant d.c. signal and thereafter is actuated step-by-step in the reverse direction until it reaches the approximate value for the required light intensity.

14. An apparatus according to claim 9, wherein said computer means is operable to determine the dependence of the in-phase signal on the pump modulating frequency to obtain information about electric field distributions and trap times.

15. A method for obtaining information about trap times, especially at interfaces of semiconductors and semiconductor heterostructures, comprising the steps of
   a) directing a probe beam of monochromatic light onto a material sample whose characteristics are to be determined,
   b) electromodulating the sample by directing onto the same a pump beam from a pump source acousto-optically modulated with a frequency above that attainable by mechanical modulation to obtain information about trap states with relatively short time constants,
   c) collecting the light reflected from or transmitted by the sample in a detector which produces a d.c. signal and an a.c. signal containing an in-phase component, and
   d) determining the dependence of the in-phase photoreflectance signal on the acousto-optical pump modulating frequency to obtain information about trap times.

16. A method according to claim 15, further comprising the step of obtaining information about multiple trap states from step d).

17. A method according to claim 16, wherein the variation of the frequency of the acousto-optical pump beam modulation and the accumulation of the in-phase component of the signal are obtained by computer control.

18. A method for obtaining information about identification of component layers and their quality and about the properties of the respective interfaces of semiconductors and semiconductor heterostructures, comprising the steps of
   a) directing a probe beam of monochromatic light onto a material sample,
   b) electromodulating the sample by directing onto the same a pump beam from a pump source,
   c) collecting the light reflected from or transmitted by the sample in a detector which produces a d.c. signal and an a.c. signal, and
   d) varying the wavelength of the pump beam and the modulating frequency thereof.

19. A method according to claim 18, wherein the modulating frequency of the pump beam is varied up to a maximum value of about at least 100 kHz by acousto-optical modulation.

20. A method according to claim 19, further comprising the step of determining the dependence of the in-phase signal on the pump modulating frequency to obtain information about trap times.

* * * * *